United States Patent
Lee et al.

(10) Patent No.: US 7,622,132 B2
(45) Date of Patent: Nov. 24, 2009

(54) ENCAPSULATED COSMETIC COMPOSITION

(75) Inventors: Wilson An-Tuen Lee, Hauppauge, NY (US); Leigh Andersen Silveira, Ronkonkoma, NY (US)

(73) Assignee: ELC Management, LLC, New York, NY (US)

( * ) Notice: Subject to any disclaimer, the term of this patent is extended or adjusted under 35 U.S.C. 154(b) by 103 days.

(21) Appl. No.: 11/425,446

(22) Filed: Jun. 21, 2006

(65) Prior Publication Data

US 2006/0292193 A1 Dec. 28, 2006

Related U.S. Application Data

(60) Provisional application No. 60/694,312, filed on Jun. 27, 2005.

(51) Int. Cl.
*A61K 8/02* (2006.01)
(52) U.S. Cl. .................. 424/401; 424/61; 424/451; 424/455
(58) Field of Classification Search ............ None
See application file for complete search history.

(56) References Cited

U.S. PATENT DOCUMENTS

| | | | | |
|---|---|---|---|---|
| 4,927,687 | A | * | 5/1990 | Nuwayser ............ 424/449 |
| 5,532,000 | A | * | 7/1996 | Kauffmann ............ 424/450 |
| 5,648,095 | A | * | 7/1997 | Illum et al. ............ 424/489 |
| 5,674,504 | A | * | 10/1997 | Kauffmann ............ 424/401 |
| 6,174,466 | B1 | | 1/2001 | Kiefer et al. |
| 6,455,056 | B1 | | 9/2002 | Franklin et al. |
| 6,572,892 | B1 | | 6/2003 | Ioulalen et al. |
| 2008/0089913 | A1 | * | 4/2008 | Kallmayer et al. ........ 424/401 |

FOREIGN PATENT DOCUMENTS

EP 0 720 472 B1 * 7/1999
JP 08040828 A * 2/1996

OTHER PUBLICATIONS

Robert F. Jimerson; Soft Gelatin Capsule Update; Drug Development and Industrial Pharmacy, (Interphex "86 Conference), vol. 12 No. 8&9, pp. 113-114 (1986).
P.K. Wilkerson&F.S.Song;Softgels: Manufacturing Considerations,Drugs and the Pharmacuetical Sci. 41(Specialized Drug Systems),P.Tyle,Ed.(Marcel Dekker, Inc., NY'90)pp. 409-449.
Patel, Morton, & Seager; "Advances in Softgel Formulation Technology", Manufacturing Chemist, vol. 60, No. 7, pp. 26-28 (Jul. 1989).
Patel, Morton & Seager; "Softgel Technology"; Manufacturing Chemist, vol. 60, No. 8, pp. 47-49 (Aug. 1989).
William R. Ebert, "Soft Elastic Gelatin Capsules: A Unique Dosage Form", Pharmaceutical Technology, vol. 1, No. 5, pp. 44-50 (1977).
F.S. Horn et al., "Capsules, Soft", Encyclopedia Of Pharmaceutical Technology, vol. 2, J. Swarbrick & J.C. Boylan, eds.(Marcel Dekker, Inc., NY 1990) p. 269-284.
Tamara Smith& Shionogi Qualicaps;The Hard Capsules with the Soft Center; The Re-Emergence of Liquid-Filled Hard Capsules; Tablets & Capsules CSC Publishing, Jan. 2004.
Royal Pharmacuetical Society of Great Britian Information Sheet:9; Capsules and Tablets (C)P G Homan, FRPharmS MCpp,2002.
PCT International Search Report; International Application No. PCT/US06/024521; Completion Date: Dec. 6, 2006; Date of Mailing: Dec. 7, 2006.
PCT Written Opinion Of the International Searching Authority, Or The Declaration; International Application No. PCT/US06/024521; Completion Date: Dec. 6, 2006; Mailing Date: Dec. 7, 2006.

\* cited by examiner

*Primary Examiner*—Sreeni Padmanabhan
*Assistant Examiner*—Layla Soroush
(74) *Attorney, Agent, or Firm*—Peter Giancana

(57) ABSTRACT

The present invention relates to encapsulated cosmetic compositions that are topically applied. The compositions contain at least one frangible capsule that has a seamless shell of a thermo-softening material. The shell is solid at about room temperature and melts upon application to the skin. The shell holds a core cosmetic that is added to a clear gel base. Thus, the color of the capsule is visible and multiple colored capsules can be added to the base for a custom colored composition.

21 Claims, No Drawings

ENCAPSULATED COSMETIC COMPOSITION

This application claims priority of U.S. 60/694,312, filed Jun. 27, 2005.

FIELD OF THE INVENTION

The invention relates to encapsulated cosmetic compositions, especially foundation. More specifically, the invention relates to any type of cosmetic compositions that are encapsulated and suspended in a cosmetically acceptable vehicle to provide custom color.

BACKGROUND OF THE INVENTION

The application of decorative or masking colors to the skin of humans and particularly to match the color applied to the face of humans is a highly specialized technical area. The color of the composition can vary greatly between the appearance of the color of the actual composition and the appearance of the color as applied depending upon the specific location to which the color is to be applied. For example, the compositions used to apply color to the lips (e.g., lipstick or lip balm) are affected by the pink or reddish background color of the lips. Mascara in colors other than black must have very high color density to counter the color of the eyelashes, especially black or brown colored eyelashes. Rouge and eye shadow must also be capable of providing color against various skin tones. While bases and foundation colors would seem to be less difficult because they are close in color to the skin to which they are applied, the technicality of matching the color of the foundation to that of the skin of unique coloration is many times more challenging than with any other type makeup. Consumers expect the foundation or base color to match their skin exactly so that it does not appear as though they are wearing foundation. Traditionally, a discrete set of colors are developed for application on skin color of consumers, no two of which are the same.

Beauty advisors typically recommend blending two or more colors to achieve the specific desired color for the skin. However, there are some disadvantages to the consumer involved in blending foundation colors. First, the consumer is now put in a position of having to purchase two products instead of one. Further, the two products require additional storage space either in the home or in the cosmetic bag. And finally, the consumer must take extra time to blend and apply the two colors to create the final desired color for their skin. In recent years, even decades, time has become a more widely recognized and valued commodity. Therefore, many consumers do not find the recommendation of blending colors a satisfactory one. There is therefore a need to offer unique foundation colors that the consumer can customize and purchase only the amount they need and desire. The present invention provides such cosmetic compositions, especially foundation compositions which provide custom color to the consumer.

SUMMARY OF THE INVENTION

The present invention relates to topically applied compositions containing at least one frangible capsule encapsulating a core cosmetic composition. The capsules are suspended in a cosmetically acceptable base or vehicle and have a seamless shell composed of a thermo-softening material that is solid at about room temperature and that melts upon application to the skin. The shell forms the outer wall of the capsule and encapsulates a core cosmetic material which is the cosmetic composition. Due to the thermo-softening nature of the material, the shell is solid and self supporting at about room temperature and melts and ruptures upon application to the skin (about body temperature).

The core cosmetic is maintained within the capsule as it being dispensed from the product container; but upon application to the skin the core cosmetic is released from the capsule and provides color coverage when, for example, the core cosmetic is a foundation. The encapsulated core cosmetic presents a product that custom blends foundation color by combining any number of shades of capsules within the capsule composition. The foundation composition comprises a plurality of frangible capsules having a translucent or clear seamless shell. The core cosmetic is a foundation encapsulated by the shell and has at least one colorant forming a shade that is visible through the shell. There are two or more shades of frangible capsules that are present in the cosmetically acceptable base. Thus, the compositions of the present invention are useful for creating custom colored compositions. Therefore, the present invention includes methods of adding frangible capsules described above having the seamless shell and core cosmetic to a cosmetically acceptable base.

DETAILED DESCRIPTION OF THE INVENTION

The frangible capsules employed in the present invention comprise a one-piece, seamless shell composed of a thermo-softening material that is solid at about room temperature and melts upon application to the skin. These characteristics permit the capsule to maintain its integrity while it is suspended in the cosmetically acceptable vehicle and is stored in a container before use. The capsules in the compositions of the present invention must when contained in a package or container be visibly suspended as a capsule in the cosmetically acceptable vehicle. The capsule must also be self supporting under two conditions. The first condition is when the capsule is in a product container as part of the topically applied composition. The capsule in the topically applied composition must maintain its integrity during shipping and storage in a variety of situations. The second condition is as it is being dispensed as part of the composition from the package or container. Between the time the topically applied composition containing the frangible capsule is removed and applied to the skin surface, the capsule must be self supporting. Not withstanding its inherent self-supporting nature, the capsule is relatively soft upon touch. Thus, the frangible capsules of the present invention are referred to as soft capsules. The term "soft capsules" is used in the present invention generally as the term of art is understood except that it must meet the certain criteria. First, it must melt at body temperature immediately upon rubbing; and second, it must pass shipping test, e.g., stability of product under temperature and shaking conditions. In addition, it desirable if buoyancy of the capsules is achieved and maintained overtime (i.e., stable) so that they float in the final product to create a satisfying and pleasing visual effect. The capsules are designed such that both the warmth of the skin surface and the stress of being rubbed onto the skin surface are necessary for the self-supporting structure of the capsule to be overcome. Since the capsule is in a vehicle, it is cushioned and will not actually begin to melt until the product is actually rubbed into the skin.

As previously mentioned, as the capsule is removed and applied to the skin it must be self-supporting. However, this is also when the nature of the capsule must transition as it is applied topically to a warm surface such as the skin. The transition at this point entails the capsule desirably melting as a result of the warm skin temperature and rupturing due to stresses (e.g., by rubbing the composition onto the skin surface) that are applied during application of the topically applied compositions to the skin surface. Upon melting and rupturing, the cosmetic composition contained within the capsule is released onto the surface. Therefore, upon topical application to the skin, the capsules must rupture easily and function as the cosmetic composition it contains is designed to be. This is aided by the ability of the shell to melt at body temperature and under stress conditions that are typically found when applying a cosmetic composition to the skin.

The criteria of the capsule are achieved with a shell that comprises different materials each of which has a different melting point. The seamless shell is unilayer and formed of thermo-softening materials that are gelatin-free and plasticizer-free. Examples of materials that can be used in the present invention as the thermo-softening material, include but are not limited to, stearyl dimethicone, beeswax, almond butter (sweet almond oil 55%/hydrogenated vegetable oil 45%) cocoa butter, PEG-8 dimethicone, dimethicone copolyol beeswax, vinyl dimethicone, dimethicone, C-30-45 alkyl methicone, olive butter (olive fruit oil/hydrogenated olive oil), candelilla wax, and polyethylene, carnauba wax, ceresin wax, microcrystalline wax, paraffin wax, orange peel wax, lavender wax, jojoba esters, rose flower wax, synthetic beeswax, polyglyceryl-3 beeswax, ozokerite, synthetic wax, rice wax, rice bran wax, fatty acid waxes, and flower waxes. Waxes have been known to be used as the coating for the exterior of the capsule; but it is not heretofore been known as the material used to make the outer wall of the capsule per se. Thus, the thermo-softening material is the sole material used as the shell of the capsule. The shell is only one layer—it is not multi-layered. Preferably, the thermo-softening materials are waxes in a wax blend. More preferably, the waxes form a blend that contains at least a stearyl dimethicone. More preferably still, the wax blend contains at least 3 thermo-softening materials where at least one of the 3 materials is stearyl dimethicone. More preferably further still, the blend of thermo-softening materials contains in addition to the stearyl dimethicone, at least one of almond butter, cocoa butter, PEG-8 dimethicone or beeswax. In which case, the components are present in the following amounts, stearyl dimethicone 15 to 60 percent, beeswax 10 to 20 percent, almond butter (sweet almond oil hydrogenated vegetable oil) 10 to 20 percent, cocoa butter 10 to 50 percent, PEG-8 dimethicone 10 to 20 percent.

The melting point of the wax blend used to make the shell contributes to the ability of the shell to melt upon topical application to the skin. Thus, the desirable melting point of the wax blend is based upon the temperature required to melt upon topical application to the skin. Preferably, the melting point of the wax blend is in the range of between 30 and 50 degrees Celsius (° C.). More preferably, the melting point of the wax blend is between 37° C. and 45° C. The viscosity of the wax blend is about 3000 to 5000 poise at about one reciprocal second using a standard rheometer, for example, TA Instrument, AR2000 Rheometer, Geometry: 20 mm 4° steel cone with 82 μm gap, and applying a controlled shear stress test, where shear stress is ramped from 0 to 10000 dyne/cm$^2$ in 5 minutes at a controlled temperature at 37° C. during the test.

The shell is seamless as a result of forming by a freezing process. The process of freezing in the present invention is a quick chilling process that is distinguishable from freeze-drying because it does not involve the removal of water from the shell. The shell materials are free of water, and therefore, there is no need for the step of drying to remove water. The thermo-sensitive material is such that when exposed to certain freezing/chilling conditions the thermo-softening material forms the outer shell of the capsule. Examples of similar freeze drying/quick chilling process are described in for example, U.S. Pat. No. 6,174,466 incorporated herein by reference, and other similar methods known in the art. The seamless shell of the present invention has a thickness between 2 and 20 microns. The frangible capsule has a particle size in the range of between 500 to 1500 microns, and is preferably about 500 to 1000 microns. The capsules are like a bubble or small bead and are approximately round or teardrop in shape. In a preferred embodiment, the seamless shell is prepared with air bubbles to support the buoyancy of the frangible capsule in the cosmetically acceptable base. Various amounts of air bubbles are created in the seamless shell thickness so that the final frangible capsules are suspended at varying heights in the cosmetically acceptable base.

The frangible capsules are suspended in a cosmetically acceptable base or vehicle. Depending on the amount of capsules added to the vehicle, the coverage achieved by the makeup as a final product can vary from a sheer (light) coverage to a greater coverage for blemishes, dark circles and the like. Thus, the amount of capsules added to the vehicle is about 1 to 40 percent by weight of the composition. In addition, to the level of coverage, there is also the desired shade of color that must be determined and based on both the final shade of color and the amount of coverage the amount of capsules for the final product is determined. The capsules are simply added to the vehicle and blended together with mild agitation. The final product, the encapsulated cosmetic composition of the present invention, is poured into an appropriate container for storage and dispensing.

Preferably the base is translucent or clear. More preferably, the base is a clear gel. Suitable clear gels include but are not limited to carbomer gels, silicone gels, polyacrylamide gels, polyquaternium 37, hydroxypropyl starch, hydroxyethyl cellulose, hydroxypropyl methylcellulose, hydroxypropyl cellulose. The clarity of the capsule shell, and therefore, the capsule itself, permits the individual shades of the frangible capsules in the cosmetic composition, especially in the case of a foundation, to be observed by the consumer. The visibility of the individual shades of the capsules provides an aesthetically pleasing product and it gives the consumer an idea of what the product may look like when it is blended to make the custom color. Various shades of the core cosmetic, especially foundation, are contained within individual capsules and upon application blend to make one custom color. Like dots in a Georges Seurat neo-impressionist painting, the diversely colored capsules present in the clear gel base portray an estimation of the desired blended custom color. Thus, the composition contains a plurality of frangible capsules having two or more shades. Within the capsules, the core cosmetic comprises at least one colorant to form a shade. Each capsule has a different shade of the core cosmetic. As a result, individual frangible capsules have various shades based on the shade of the core cosmetic contained therein. When a plurality of frangible capsules having two or more shades are added to the cosmetically acceptable base, the custom color is created.

The method of creating a custom blend makeup product starts with the clear gel base. The consumer chooses capsules of various shades that are believed or known to combine and blend into a shade that matches their skin tone. The various shades of foundation containing capsules are added to the clear gel base, and upon application of the product the capsules melt and rupture to release the foundation. Consequently, the consumer can match their skin color as closely as possible with one product, namely, the composition of the present invention containing the different shades of cosmetic containing capsules in the clear gel base.

The core cosmetic contains at least one colorant forming a shade. A colorant as used in the present specification is any cosmetically acceptable pigment that is organic, inorganic, water soluble or water insoluble, or any cosmetically acceptable dye, or combinations thereof. Examples of useful inorganic pigments include iron oxides (yellow, red, brown or black), ferric ammonium ferrocyanide (blue), manganese violet, ultramarine blue, chrome oxide (green), talc, lecithin modified talc, zeolite, kaolin, lecithin modified kaolin, titanium dioxide (white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof.

Also included are copolymer pigments that are water insoluble, e.g., nylon powder, polyethylene, and polyesters. The polyesters can include linear, thermoplastic, crystalline or amorphous materials produced using one or more diols and one or ore dicarboxylic acids copolymerized with colorants. Pigment concentrations will vary depending upon the color of the final product, but generally will be in the range of from about 0.1-20% by weight of the total composition.

The core cosmetic is any cosmetic composition that is intended to be encapsulated and added to the final product type. Examples of suitable core cosmetics include but are not limited to fluid products such as foundations, sunscreens, cream concealer, bronzer, blush, eyeshadow, eyeliner, mascara, and any non-stick colored lip products such as lip gloss; and powder products, such as pressed or loose powders, face powder, powder blushes, and powder eye shadows. The core cosmetic can be used in any clear gel base in which a pigment would be necessary or desirable, by simply adding the capsule containing the core cosmetic to the clear gel base.

Preferably, the core cosmetic is a foundation. The core cosmetic, including the foundation, can be any type of emulsion, for example, oil-in-water, water-in-oil, multi-phase emulsions, gels, or it can be anhydrous. Preferably, the core cosmetic is in the form of an oil-in-water emulsion.

The capsule compositions can also be used in any type of skin treatment product in combination with the capsule compositions containing the core cosmetic. Skin treatment products that can be encapsulated, include but are limited to cream lip products, acne treatments, moisturizers, anti-aging products, lifting treatments, cellulite treatments and eye treatments. In the case of applying the present invention to treatment products used in conjunction with makeup products, the treatment is designed to adhere to the skin first and them follow by the makeup products. Based on the skin's higher affinity for water than oil, treatments products are designed in either water suspensions or oil-in-water systems on the one hand, while on the other hand, the makeup product is designed in either anhydrous or water-in-oil systems. Thus, the compositions of the present invention can have a dual function. Some capsules hold a core cosmetic and other capsules hold a core active agent. This combination of encapsulated makeup and encapsulated active within the encapsulated cosmetic composition of the present invention can save the consumer from multiple applications of different products. Many women apply treatment products containing actives and makeup on a daily basis. In some cases the number of applications layered on the skin surface can reach as high as 6, 7 or even more. With the capsules of the present invention, a time savings can be realized by the consumer by combining capsules containing the various products added to one topically applied composition.

Accordingly, in addition to the core cosmetic, the frangible capsule can also contain a core active agent. The composition can also contain other optional components including, but not limited to, oil soluble sunscreens, such as octyl methoxycinnamate; particulate sunscreens such as Zinc Oxide; oil-soluble antioxidants and/or preservatives, such as BHT; chelating agents such as Disodium EDTA; fragrances (such as pinene); flavoring agents; waterproofing agents (such as PVP/Eicosene Copolymer); surfactants; and oil-soluble actives, such as tocopherol and its derivatives; and the like.

The invention is further illustrated by the following non-limiting examples.

Example 1

| Gel Base According to the Present invention | |
|---|---|
| Carbomer | 55.00 |
| Disodium EDTA | 0.05 |
| Phenoxyethanol | 0.73 |
| Water | 42.53 |
| Tromethamine | 1.50 |
| Chlorophenesin | 0.20 |

The carbomer (Carbopol 980) is added to a main vessel. While mixing with prop agitation, EDTA and phenoxyethanol are added to the main vessel and mixed until uniform. Tromethamine (Tris Amino) and chlorophenesin are premixed in water and added to the main vessel. When the mixture of ingredients becomes too viscous for prop agitation, the agitation is switched to side wiping agitation and mixed until uniform. The gel base is ready for addition of capsules according to the present invention.

Example 2

| Shell according to the Present Invention |
|---|
| Stearyl dimethicone - 60% |
| Almond butter - 20% |
| Beeswax - 20% |

The ingredients are put into a vessel, heated to about 60° C. and mixed with prop agitation until the batch is uniform. The uniform material is poured into a storage container and allowed to cool to room temperature. The shell can be reheated as necessary to make capsules of the present invention.

Example 3

| Exemplary Core cosmetic for encapsulating according to the Present Invention | |
|---|---|
| Phase I | |
| Water | 20.00 |
| Magnesium aluminum silicate | 0.50 |
| Phase II | |
| Propylene glycol | 1.30 |
| Cellulose gum | 0.20 |
| Xanthan gum | 0.10 |
| Phase III | |
| Methyl paraben | 0.30 |
| Sodium dehydroacetate | 0.30 |
| Steareth-20 | 0.25 |
| Trisodium EDTA | 0.05 |
| Triethanolamine | 1.70 |
| Phase IV | |
| Water | 30.00 |
| Propylene glycol | 2.50 |
| Phase V | |
| Titanium dioxide | 14.50 |
| Iron oxides | 2.20 |
| Talc | 3.00 |
| Aluminum hydroxide | 0.30 |
| Phase VI | |
| Water | 2.30 |
| Cyclopentasiloxane | 13.60 |
| Stearic acid | 2.25 |
| Glyceryl stearate | 1.50 |
| Steareth-2 | 0.25 |
| Isostearic acid | 1.25 |
| Propyl paraben | 0.10 |
| Polyethylene | 0.25 |
| Phase VII | |
| Water | 1.00 |
| Imidazolidinyl urea | 0.30 |

Add Phase I ingredients to main vessel, mix for about 10 minutes under agitation, and begin heating the vessel to about 68° C. Phase II ingredients are premixed, added to the vessel and mixed for 10 minutes. Add Phase III ingredients to the vessel and mix for 10 minutes. Premix Phase IV and Phase V ingredients and pass them through a ball mill. Rinse the milled ingredients with the water in Phase VI. The milled Phase IV and V ingredients including the water from Phase VI are added to the vessel and mixed for 10 minutes. In a separate vessel, the remaining Phase VI ingredients except for the cyclopentasiloxane are mixed and heated to about 95° C. until uniform. Prior to emulsification the cyclopentasiloxane is added and the mixture is maintained at 75° C. The ingredients in the separate vessel are added to the main vessel, and mixed for 30 minutes. The ingredients are cooled to about 30° C. Phase VII ingredients are premixed and added to the vessel when the temperature reaches about 40° C. The cosmetic core is prepared and ready for encapsulation according to the present invention.

Example 4

Capsules According to the Present Invention

Two phases are required. One phase consists of the shell prepared in Example 2 and the other consists of the core cosmetic prepared in Example 3 to be encapsulated within the shell. Using an apparatus which has two nozzles, one inside of the other, the inner nozzle delivers the core cosmetic and the outer nozzle delivers the shell. The thickness and size/shape of the particles is determined by the size of the nozzles, the distance between the inner and outer nozzle and the freezing rate determined by the freezing temperature. The two phases are dispensed into a tube of a certain length, about 1 to 2 feet, which is chilled at a certain temperature of about −20° C. to 0° C. As the phases are dispensed they form droplets. As the droplets fall down the tube the shell is quickly frozen entrapping the core cosmetic. The capsule is formed with the core cosmetic encapsulate by the shell.

Example 5

Encapsulated Cosmetic Composition According to the Present Invention

| | |
|---|---|
| Gel base of Example 1 - 75% | |
| Capsules of Example 4 - 25% | |

Add capsules to gel base and blend together with mild agitation to form encapsulated cosmetic composition according to the present invention.

What we claim is:

1. A topically applied composition comprising:
    at least one frangible capsule having a seamless shell of a thermo-softening material that is solid at about room temperature, that will rupture when the composition is rubbed on a skin surface, and that melts upon application to the skin wherein said thermo-softening material is gelatin free and plasticizer-free;
    a core cosmetic encapsulated by the seamless shell, the core cosmetic having a shade that is visible through the shell; and
    a cosmetically acceptable base containing the frangible capsule suspended therein.

2. The composition of claim 1 in which said thermo-softening material is a wax blend.

3. The composition of claim 2 wherein said wax blend comprises at least one stearyl dimethicone.

4. The composition of claim 3 wherein said wax blend further comprises a wax selected from beeswax, almond butter (sweet almond oil—55%/hydrogenated vegetable oil—45%), cocoa butter, PEG-8 dimethicone.

5. The composition of claim 1 wherein the seamless shell is unilayer.

6. The composition of claim 2 wherein said wax blend has a melting point between 30 and 50° C.

7. The composition of claim 6 wherein said wax blend has a melting point between 37 and 45° C.

8. The composition of claim 1 wherein said seamless shell has a particle size between 500 and 1500 microns.

9. The composition of claim 1 wherein said seamless shell has a thickness between 2 and 20 microns.

10. The composition of claim 1 wherein said seamless shell is formed by a freezing process.

11. The composition of claim 1 wherein said seamless shell further comprises air bubbles.

12. The composition of claim 1 wherein said cosmetically acceptable base is translucent or clear.

13. The composition of claim 11 wherein said cosmetically acceptable base is a clear gel.

14. The composition of claim 1 wherein said composition contains a plurality of frangible capsules.

15. The composition of claim 13 wherein said core cosmetic further comprises at least one colorant forming a shade.

16. The composition of claim 14 wherein each of said frangible capsules further comprises a shade of said core cosmetic.

17. The composition of claim 15 wherein said composition comprises a plurality of frangible capsules having two or more shades.

18. The composition of claim 1 wherein said core cosmetic is a foundation.

19. The composition of claim 1 further comprising:
at least one frangible capsule having a seamless shell of a thermo-softening material that is solid at about room temperature, that will rupture when the composition is rubbed on a skin surface, and that melts upon application to the skin; and
a skin treatment active encapsulated by the seamless shell.

20. A method of creating a custom colored topically applied composition which comprises the steps of suspending in a cosmetically acceptable base, frangible capsules that have:
a seamless shell of a thermo-softening material that is solid at about room temperature and that melts upon application to the skin wherein said thermo-softening material is gelatin free and plasticizer-free; and
a core cosmetic.

21. A foundation composition comprising a plurality of frangible capsules having a translucent or clear seamless shell of a thermo-softening material that is solid at about room temperature and that melts upon application to the skin wherein said thermo-softening material is gelatin free and plasticizer-free and having a core foundation encapsulated by the seamless shell comprising at least one colorant forming a shade visible through the seamless shell, said frangible capsules being present in two or more shades and being suspended in a cosmetically acceptable base.

* * * * *